US012029601B2

(12) United States Patent
Cao et al.

(10) Patent No.: US 12,029,601 B2
(45) Date of Patent: Jul. 9, 2024

(54) SYSTEMS AND METHODS FOR THREE-DIMENSIONAL IMAGING (71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 276 days.

(21) Appl. No.: 17/571,889

(22) Filed: Jan. 10, 2022

(65) Prior Publication Data

US 2022/0125397 A1    Apr. 28, 2022

Related U.S. Application Data (63) Continuation of application No. PCT/CN2019/098158, filed on Jul. 29, 2019.

(51) Int. Cl.
*A61B 6/50* (2024.01)
*A61B 6/00* (2006.01)
(Continued)

(52) U.S. Cl.
CPC ............ *A61B 6/50* (2013.01); *A61B 6/4266* (2013.01); *A61B 6/485* (2013.01); *G01N 33/5091* (2013.01)

(58) Field of Classification Search
CPC ......... A61B 6/50; A61B 6/4266; A61B 6/485; A61B 5/0071; A61B 6/025; A61B 6/037;
(Continued)

(56) References Cited

U.S. PATENT DOCUMENTS 4,179,100 A * 12/1979 Sashin ................ G01T 1/20186
378/146
5,846,513 A    12/1998 Carroll et al.
(Continued)

FOREIGN PATENT DOCUMENTS

| CN | 105520742 A | 4/2016 |
| WO | 2014045045 A1 | 3/2014 |
| WO | 2015164487 A1 | 10/2015 |

OTHER PUBLICATIONS

Rizzo et al., "Metastatic and non-metastatic lymph nodes: quantification and different distribution of iodine uptke assed by dual-energy CT," European Society of Radiology, vol. 28, pp. 760-769. (Year: 2007).*

(Continued)

*Primary Examiner* — Kiho Kim
(74) *Attorney, Agent, or Firm* — IPRO, PLLC; Qian Gu (57) ABSTRACT Disclosed herein is a method, comprising: introducing a tracer into a body region of an organism at an introduction site of the organism; causing emission of characteristic X-rays of the tracer in the body region; capturing images of the tracer in the body region with the characteristic X-rays; determining a first three-dimensional (3D) distribution of the tracer in the body region based on the images; and examining the first 3D distribution of the tracer in the body region to identify a sentinel lymph node for the introduction site. If the sentinel lymph node is not identified in the first 3D distribution, the method further comprises repeating said causing, said capturing, and said determining thereby resulting in a second 3D distribution of the tracer in the body region; and examining the second 3D distribution to identify the sentinel lymph node.

10 Claims, 12 Drawing Sheets

(51) Int. Cl.
*A61B 6/42* (2024.01)
*G01N 33/50* (2006.01)

(58) Field of Classification Search
CPC ..... A61B 6/4057; A61B 6/4275; A61B 6/508; A61B 6/502; A61B 6/4435; A61B 6/4233; A61B 6/4291; A61B 6/466; A61B 6/5205; A61B 6/5235; A61B 6/06; A61B 6/4064; A61B 6/481; A61B 6/501; A61B 6/5241; G01N 33/5091; G01T 1/161

See application file for complete search history.

(56) References Cited

U.S. PATENT DOCUMENTS

| | | |
|---|---|---|
| 2008/0253637 A1* | 10/2008 | Boyden .................. A61B 6/145 382/131 |
| 2009/0234202 A1 | 9/2009 | Goix et al. |
| 2010/0027866 A1 | 2/2010 | Ohi |
| 2013/0010927 A1 | 1/2013 | Seppi et al. |
| 2015/0087957 A1 | 3/2015 | Liu et al. |
| 2016/0051215 A1 | 2/2016 | Chen et al. |
| 2016/0377545 A1 | 12/2016 | Wang |
| 2017/0032105 A1 | 2/2017 | Yakami et al. |

OTHER PUBLICATIONS

Ultravist, downloaded from www.accessdata.fda.gov on Dec. 5, 2023, (year: 2007).*

* cited by examiner

810: Causing the tracer in L imaging regions (i.e., slices or bars) of the object 104 to emit L characteristic X-rays and capturing L region images of the tracer in the L imaging regions with the L emitted characteristic X-rays.

820: Determining a three-dimensional (3D) distribution of the tracer in the object 104 based on the L region images.

SYSTEMS AND METHODS FOR THREE-DIMENSIONAL IMAGING

TECHNICAL FIELD

The disclosure herein relates to three-dimensional imaging.

BACKGROUND

X-ray fluorescence (XRF) is the emission of characteristic X-rays from a material that has been excited by, for example, exposure to high-energy X-rays or gamma rays. Specifically, an electron on an inner orbital of an atom of the material may be ejected, leaving a vacancy on the inner orbital if the atom is exposed to X-rays or gamma rays with photon energy greater than the ionization potential of the electron. When an electron on an outer orbital of the atom relaxes to fill the vacancy on the inner orbital, an X-ray photon (called fluorescent X-ray photon, secondary X-ray photon, or characteristic X-ray photon) is emitted. The emitted X-ray photon has a photon energy equal to the energy difference between the outer orbital and inner orbital electrons.

Figure 1A:
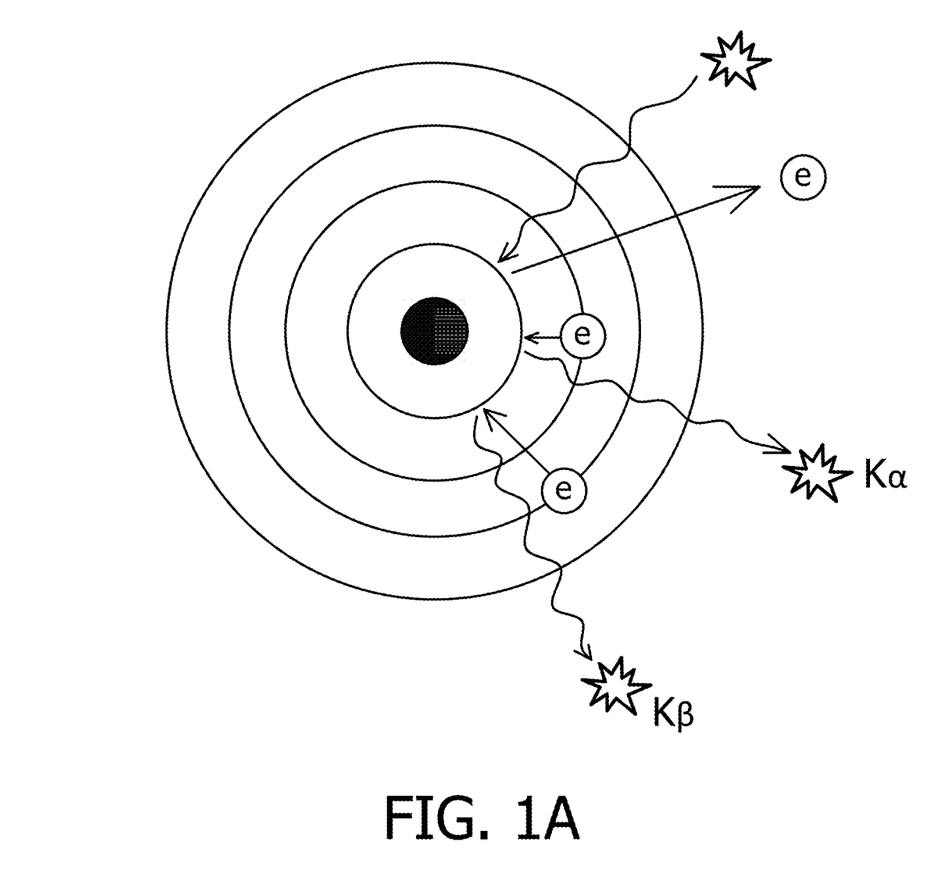
FIG. 1A and FIG. 1B schematically show mechanisms of XRF.
Figure 1B:
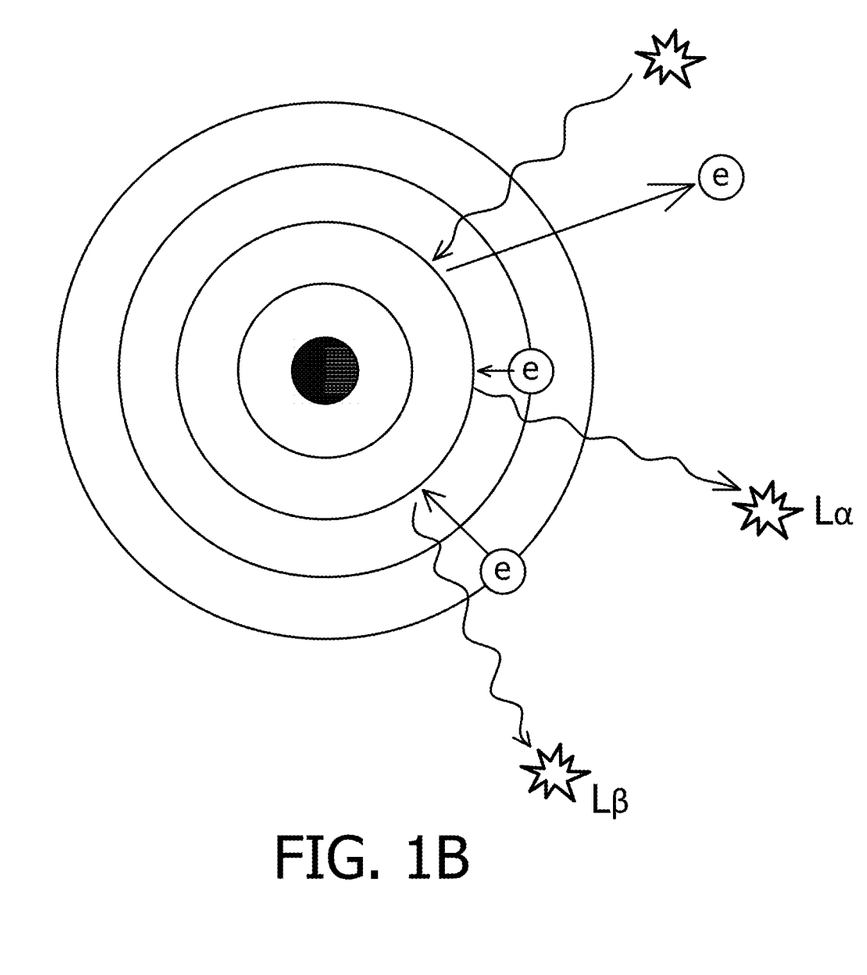

For a given atom, the number of possible relaxations is limited. As shown in FIG. 1A, when an electron on the L orbital relaxes to fill a vacancy on the K orbital (L→K), the characteristic X-ray photon is called Kα. The characteristic X-ray photon from M→K relaxation is called Kβ. As shown in FIG. 1B, the characteristic X-ray photon from M→L relaxation is called Lα, and so on.

SUMMARY

Disclosed herein is a method, comprising: introducing a tracer into a body region of an organism at an introduction site of the organism; causing emission of characteristic X-rays of the tracer in the body region; capturing images of the tracer in the body region with the characteristic X-rays, using a plurality of X-ray detectors positioned at different locations relative to the body region; determining a first three-dimensional (3D) distribution of the tracer in the body region based on the images; and examining the first 3D distribution of the tracer in the body region to identify a sentinel lymph node for the introduction site.

According to an embodiment, the method further comprises, in response to the sentinel lymph node being not identified in the first 3D distribution: repeating said causing, said capturing, and said determining thereby resulting in a second 3D distribution of the tracer in the body region; and examining the second 3D distribution of the tracer in the body region to identify the sentinel lymph node.

According to an embodiment, the method further comprises, in response to the sentinel lymph node being not identified in the second 3D distribution: repeating said causing, said capturing, and said determining thereby resulting in a third 3D distribution of the tracer in the body region; and examining the third 3D distribution of the tracer in the body region to identify the sentinel lymph node.

According to an embodiment, the introduction site is in a malignant region of the organism.

According to an embodiment, the organism is a person.

According to an embodiment, the method further comprises, in response to the sentinel lymph node being identified: removing a sample from the sentinel lymph node; and testing the sample for cancer.

According to an embodiment, the method further comprises removing additional lymph nodes surrounding the sentinel lymph node in response to cancer being found in the sample as a result of said testing.

According to an embodiment, said causing emission of the characteristic X-rays of the tracer in the body region comprises irradiating the body region with excitation radiation.

According to an embodiment, the excitation radiation comprises X-rays or gamma rays.

According to an embodiment, the tracer is non-radioactive.

Disclosed herein is a method comprising: introducing a tracer into a body region of an organism at an introduction site of the organism, wherein the body region comprises L imaging regions (imaging regions (i), i=1, . . . , L), and wherein L is an integer greater than 1; for i=1, . . . , L, causing the tracer in essentially only the imaging region (i) to emit characteristic X-ray photons (i); for i=1, . . . , L, capturing a region image (i) of the tracer in essentially only the imaging region (i) with the characteristic X-ray photons (i); determining a first 3D distribution of the tracer in the body region based on the region images (i), i=1, . . . , L; and examining the first 3D distribution of the tracer in the body region to identify a sentinel lymph node for the introduction site.

According to an embodiment, the method further comprises, in response to the sentinel lymph node being not identified in the first 3D distribution: repeating said causing, said capturing, and said determining thereby resulting in a second 3D distribution of the tracer in the body region; and examining the second 3D distribution of the tracer in the body region to identify the sentinel lymph node.

According to an embodiment, the method further comprises, in response to the sentinel lymph node being not identified in the second 3D distribution: repeating said causing, said capturing, and said determining thereby resulting in a third 3D distribution of the tracer in the body region; and examining the third 3D distribution of the tracer in the body region to identify the sentinel lymph node.

According to an embodiment, the introduction site is in a malignant region of the organism.

According to an embodiment, the organism is a person.

According to an embodiment, the method further comprises, in response to the sentinel lymph node being identified: removing a sample from the sentinel lymph node; and testing the sample for cancer.

According to an embodiment, the method further comprises removing additional lymph nodes surrounding the sentinel lymph node in response to cancer being found in the sample as a result of said testing.

According to an embodiment, said causing the tracer in essentially only the imaging region (i) to emit the characteristic X-ray photons (i) comprises irradiating imaging region (i) with excitation radiation (i).

According to an embodiment, the excitation radiation (i) comprises X-rays or gamma rays.

According to an embodiment, the tracer is non-radioactive.

Disclosed herein is a method comprising: introducing a tracer into a body region of an organism at an introduction site of the organism; causing emission of characteristic X-rays of the tracer in the body region; capturing images of the tracer in the body region with the characteristic X-rays, using a plurality of X-ray detectors positioned at different locations relative to the body region; determining a 3D distribution of the tracer in the body region based on the images; repeating said causing, said capturing, and said determining P additional times thereby resulting in a total of P+1 3D distributions of the tracer in the body region, P being a positive integer; and examining at least one 3D distribution of the P+1 3D distributions of the tracer in the body region to identify at least a sentinel lymph node for the introduction site.

Disclosed herein is a method comprising: introducing a tracer into a body region of an organism at an introduction site of the organism, wherein the body region comprises L imaging regions (imaging regions (i), i=1, . . . , L), and wherein L is an integer greater than 1; for i=1, . . . , L, causing the tracer in essentially only the imaging region (i) to emit characteristic X-ray photons (i); for i=1, . . . , L, capturing a region image (i) of the tracer in essentially only the imaging region (i) with the characteristic X-ray photons (i); determining a 3D distribution of the tracer in the body region based on the region images (i), i=1, . . . , L; repeating said causing, said capturing, and said determining Q additional times thereby resulting in a total of Q+1 3D distributions of the tracer in the body region, Q being a positive integer; and examining at least one 3D distribution of the Q+1 3D distributions of the tracer in the body region to identify at least a sentinel lymph node for the introduction site.

DETAILED DESCRIPTION

Figure 2:
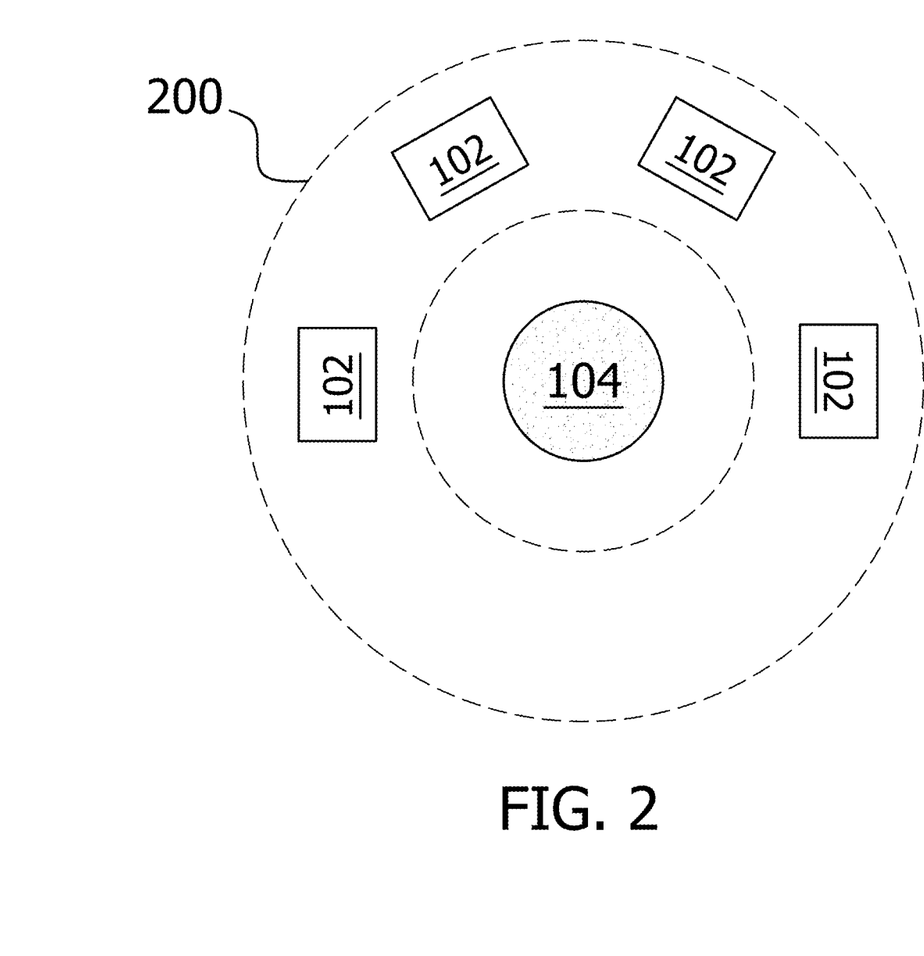
FIG. 2 schematically shows a system, according to an embodiment.

FIG. 2 schematically shows a system 200, according to an embodiment. The system 200 may include multiple X-ray detectors 102, according to an embodiment. The X-ray detectors 102 may be positioned at different locations relative to an object 104. For example, in case the object 104 is the thyroid of a person, the X-ray detectors 102 may be arranged at different locations along a semicircle around the person's neck or along the length of the person's neck.

The X-ray detectors 102 may be arranged at about the same distance or different distances from the object 104. Other suitable arrangement of the X-ray detectors 102 may be possible. The X-ray detectors 102 may be spaced equally or unequally apart in the angular direction. The positions of the X-ray detectors 102 are not necessarily fixed. For example, each of the X-ray detectors 102 may be movable towards and away from the object 104 or may be rotatable relative to the object 104.

Figure 3:
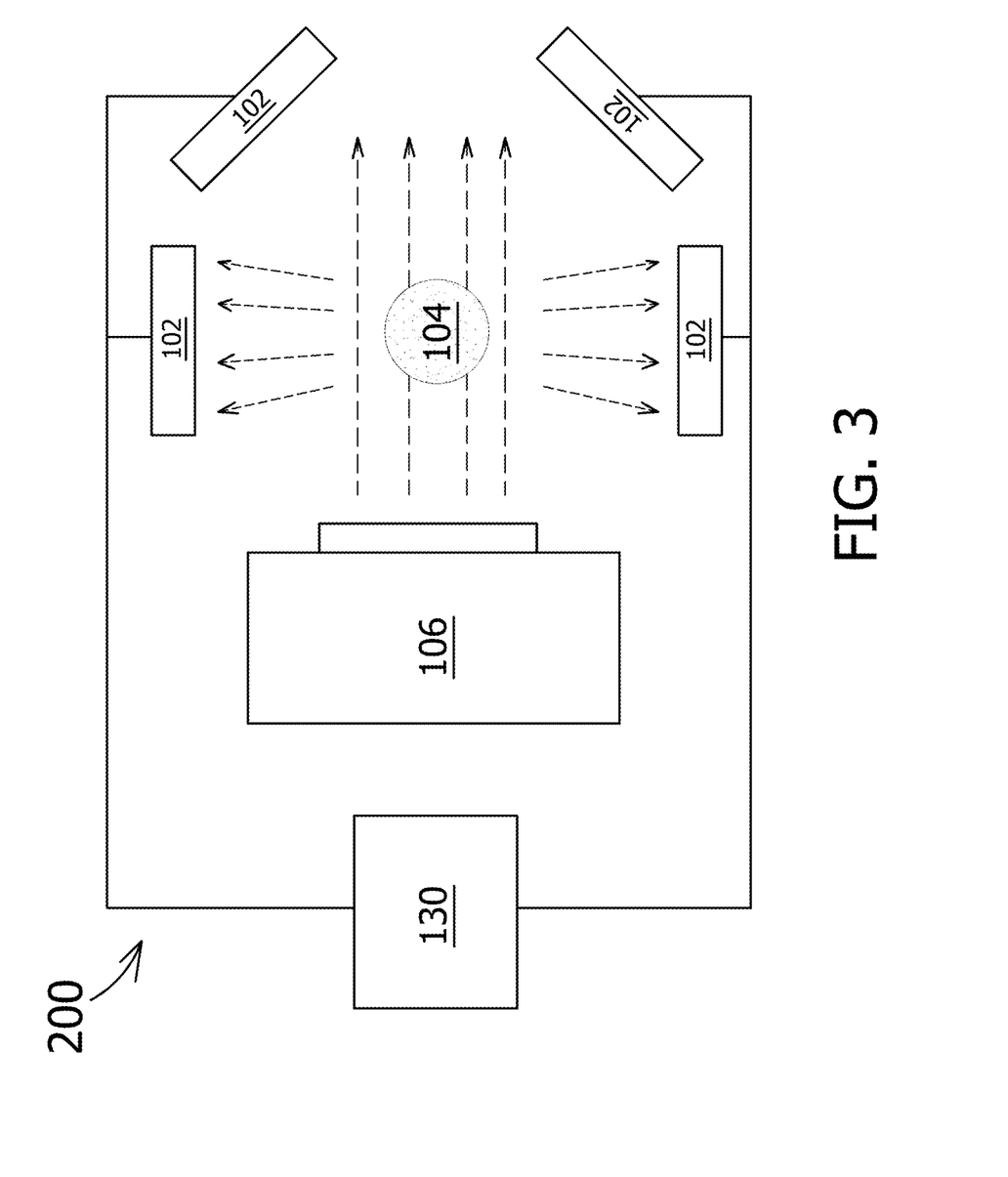
FIG. 3 schematically shows a side view of the system, according to an embodiment.

FIG. 3 schematically shows that the system 200 may include a radiation source 106, according to an embodiment. The system 200 may include more than one radiation source. The radiation source 106 may irradiate the object 104 with radiation that can cause a tracer (e.g., a chemical element) in the object 104 to emit characteristic X-rays. The tracer may be non-radioactive. The radiation from the radiation source 106 may be X-rays or gamma rays. The energies of the particles of the radiation may be in the range of 30-40 keV. The radiation source 106 may be movable or stationary relative to the object 104. The X-ray detectors 102 may capture images of the object 104 (or more specifically, the images of the tracer in the object 104) with the characteristic X-rays, (e.g., by detecting the intensity distribution of the characteristic X-rays). The X-ray detectors 102 may be disposed at different locations around the object 104 where the X-ray detectors 102 do not receive the radiation from the radiation source 106 that is not scattered by the object 104. As shown in FIG. 3, the X-ray detectors 102 may avoid those positions where they would receive radiation from the radiation source 106 that has passed through the object 104. The X-ray detectors 102 may be movable or stationary relative to the object 104.

In an embodiment, the object 104 may be a person or a portion/region (e.g., the thyroid) of a person. In an example, the object 104 may be the thyroid of a person. In this example, the tracer may be non-radioactive iodine. Non-radioactive iodine may be introduced into the person. Specifically, the person may be directed to orally take or be injected a substance containing non-radioactive iodine. The non-radioactive iodine is absorbed by the thyroid of the person. When the radiation from the radiation source 106 is directed toward the thyroid, the non-radioactive iodine in the thyroid is excited by the radiation and emits the characteristic X-rays of iodine. The characteristic X-rays of iodine may include the K lines, or the K lines and the L lines. The X-ray detectors 102 capture images of the non-radioactive iodine in the thyroid with the characteristic X-rays of iodine. In an embodiment, the X-ray detectors 102 may be configured to disregard X-rays with photon energies different from those of characteristic X-rays of iodine. Spatial (e.g., three-dimensional) distribution of the iodine in the thyroid may be determined based on these images. For example, the system 200 may include a processor 130 configured to determine the three-dimensional (3D) distribution of iodine in the thyroid based on these captured images.

Figure 4:
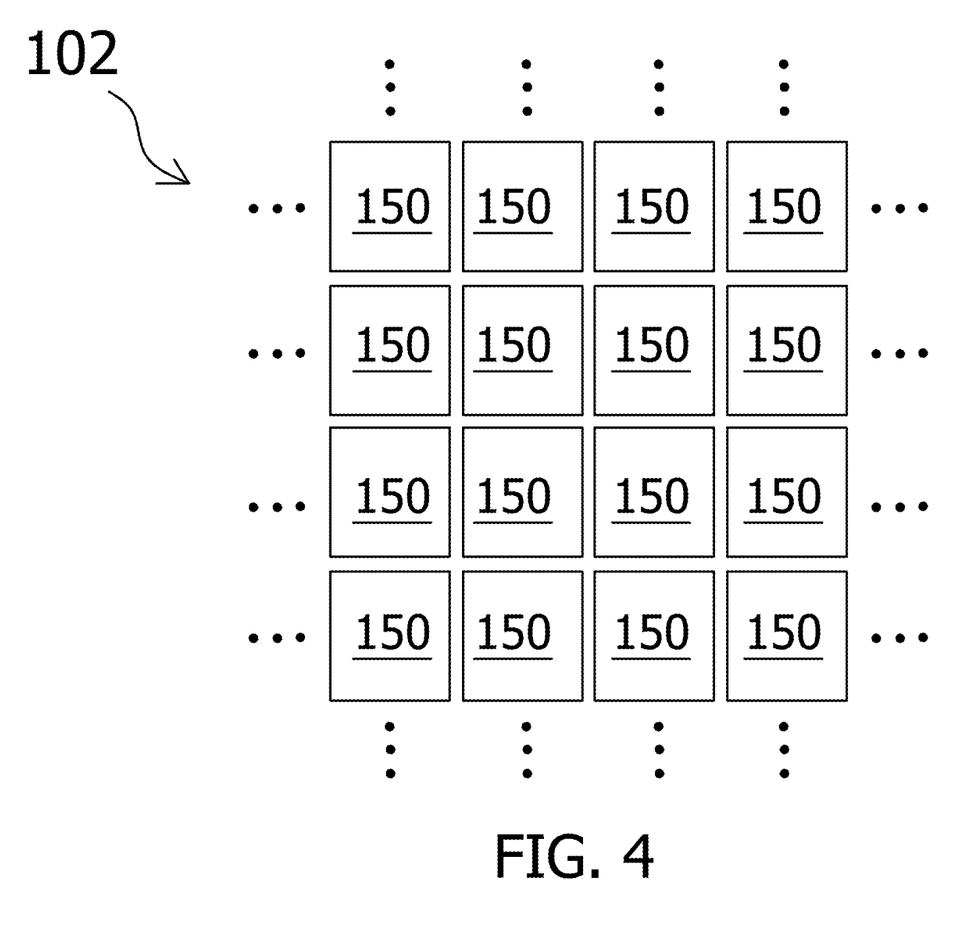
FIG. 4 schematically shows a top view of an X-ray detector of the system, according to an embodiment.

FIG. 4 schematically shows a top view of an X-ray detector 102, according to an embodiment. The X-ray detector 102 may have an array of sensing elements 150 (also referred to as the pixels 150. The sensing element array may be a rectangular array, a honeycomb array, a hexagonal array or any other suitable array. Each sensing element 150 may be configured to count numbers of photons of X-rays (e.g., the characteristic X-rays of iodine) incident on the sensing element 150 within a period of time. The sensing elements 150 may be configured to operate in parallel. For example, when one sensing element 150 measures an incident X-ray photon, another sensing element 150 may be waiting for an X-ray photon to arrive.

The sensing elements 150 may not have to be individually addressable. Each of the X-ray detectors 102 may be configured to count the numbers of X-ray photons within the same period of time. Each sensing element 150 may be able to measure its dark current, such as before or concurrently with receiving each X-ray photon. Each sensing element 150 may be configured to deduct the contribution of the dark current from the energy of the X-ray photon incident thereon.

Figure 5:
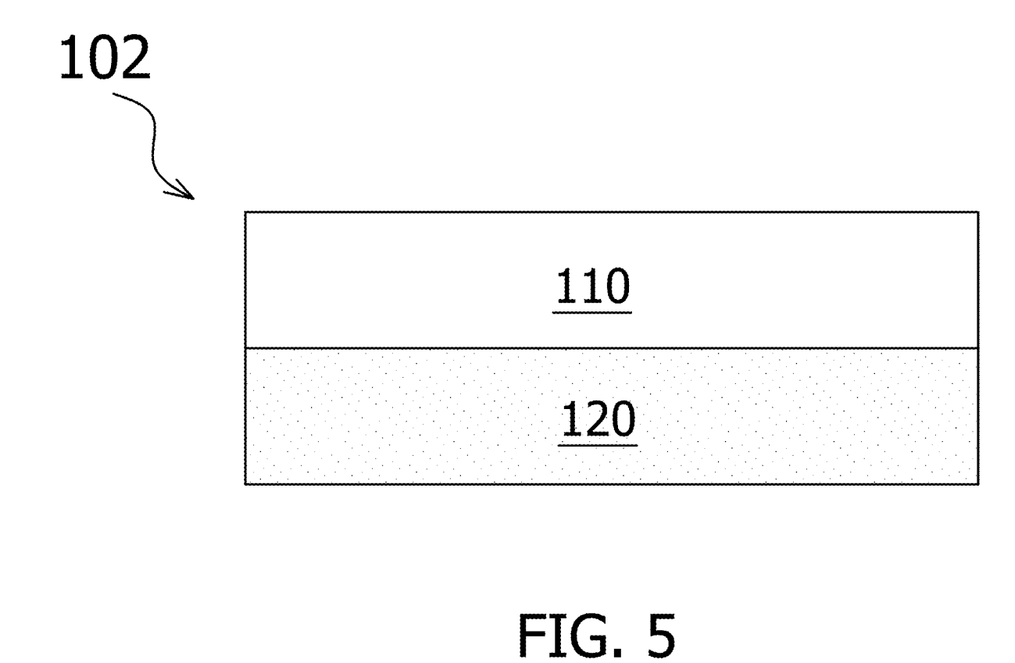
FIG. 5 schematically shows a simplified cross-sectional view of the X-ray detector, according to an embodiment.

FIG. 5 schematically shows a simplified cross-sectional view of the X-ray detector 102, according to an embodiment. The X-ray detector 102 may include an X-ray absorption layer 110 configured to generate electrical signals responsive to X-rays incident thereon. In an embodiment, the X-ray absorption layer 110 may include the sensing elements 150 (FIG. 4). In an embodiment, the X-ray detector 102 does not comprise a scintillator. The X-ray absorption layer 110 may comprise a semiconductor material such as, silicon, germanium, GaAs, CdTe, CdZnTe, or a combination thereof.

The X-ray detector 102 may include an electronics layer 120 for processing or analyzing the electrical signals which incident X-ray photons generate in the X-ray absorption layer 110. The electronics layer 120 may be integrated with the absorption layer 110 into the same chip. Alternatively, the electronics layer 120 may be constructed on a separate semiconductor wafer different from the absorption layer 110 and bonded to the absorption layer 110.

Figure 6:
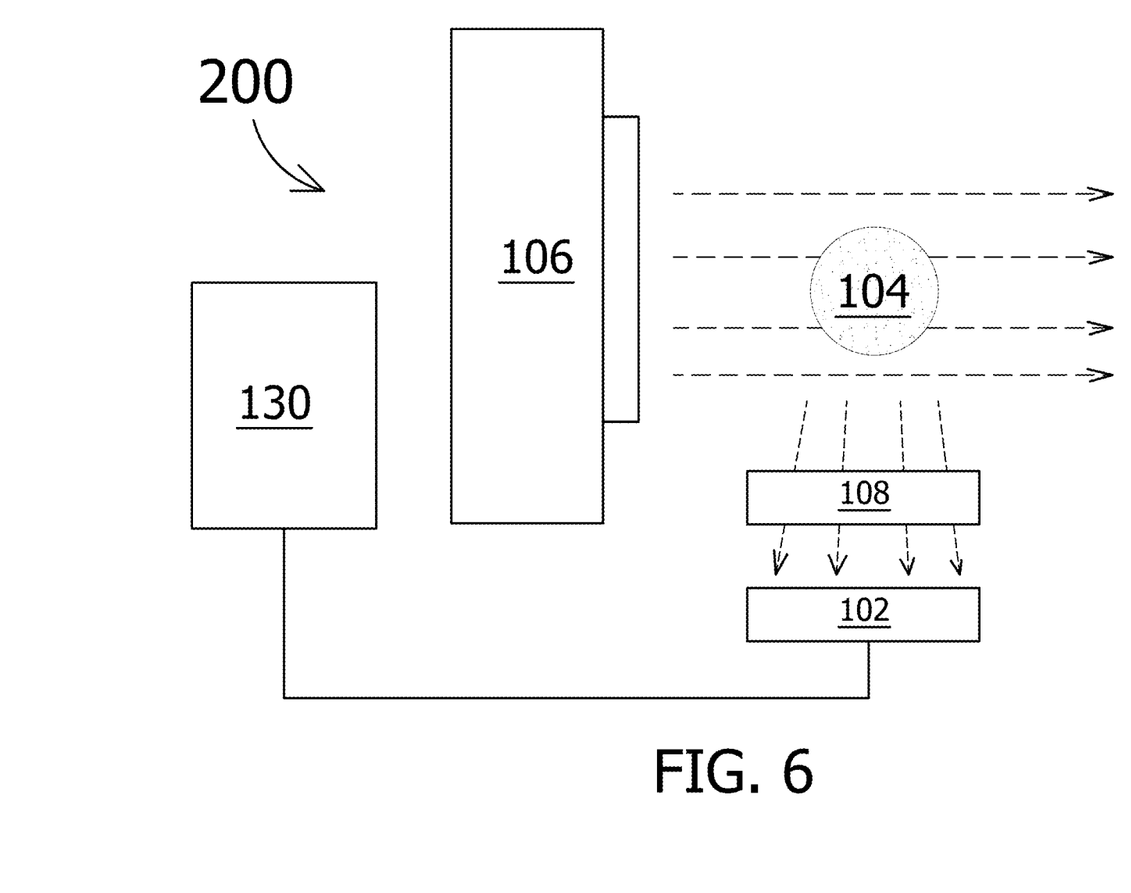
FIG. 6 schematically shows that the system may include a collimator, according to an embodiment.

FIG. 6 schematically shows that the system 200 may include a collimator 108, according to an embodiment. Only one detector 102 is shown for simplicity. The collimator 108 may be positioned between the object 104 and the detector 102. The collimator 108 may be configured to limit fields of view of the sensing elements 150 of the detector 102. For example, collimator 108 may allow only X-rays with certain angles of incidence to reach the sensing elements 150. The range of angles of incidence may be <=0.04 sr, or <=0.01 sr.

The collimator 108 may be affixed on the detector 102 or separated from the detector 102. There may be spacing between the collimator 108 and the detector 102. The collimator 108 may be movable or stationary relative to the detectors 102. The system 200 may include more than one collimator 108 (e.g., one collimator 108 for each detector 102).

Figure 7:
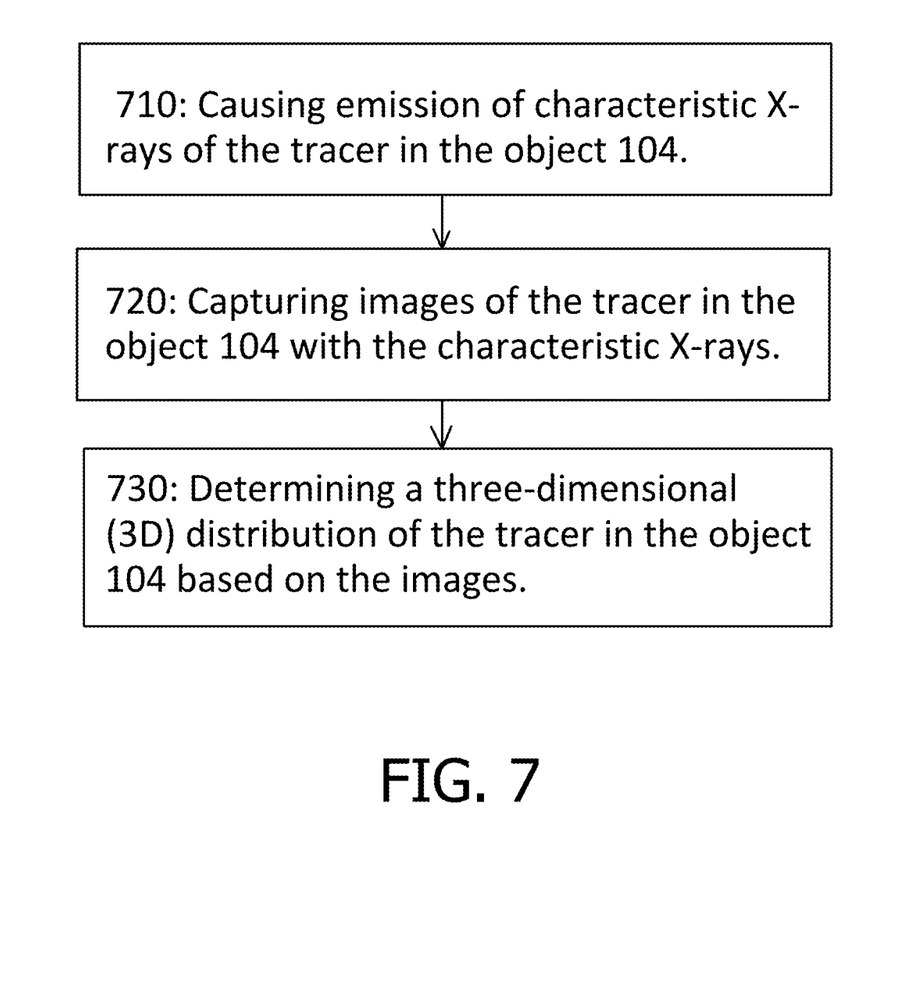
FIG. 7 shows a flowchart for a first imaging method, according to an embodiment.

FIG. 7 shows a flowchart summarizing and generalizing a first imaging method according to some embodiments described above. In step 710, emission of characteristic X-rays of the tracer in the object 104 may be caused. For example, the emission of the characteristic X-rays may be caused by irradiating the object 104 with radiation that has sufficiently high energy. The radiation may be X-rays or gamma rays. In step 720, images of the tracer in the object 104 may be captured with the emitted characteristic X-rays. For example, the X-ray detectors 102 positioned at different locations relative to the object 104 may be used to capture these images. In step 730, a three-dimensional (3D) distribution of the tracer in the object 104 may be determined based on the captured images. This step 730 may be performed using the processor 130.

Figure 8A:
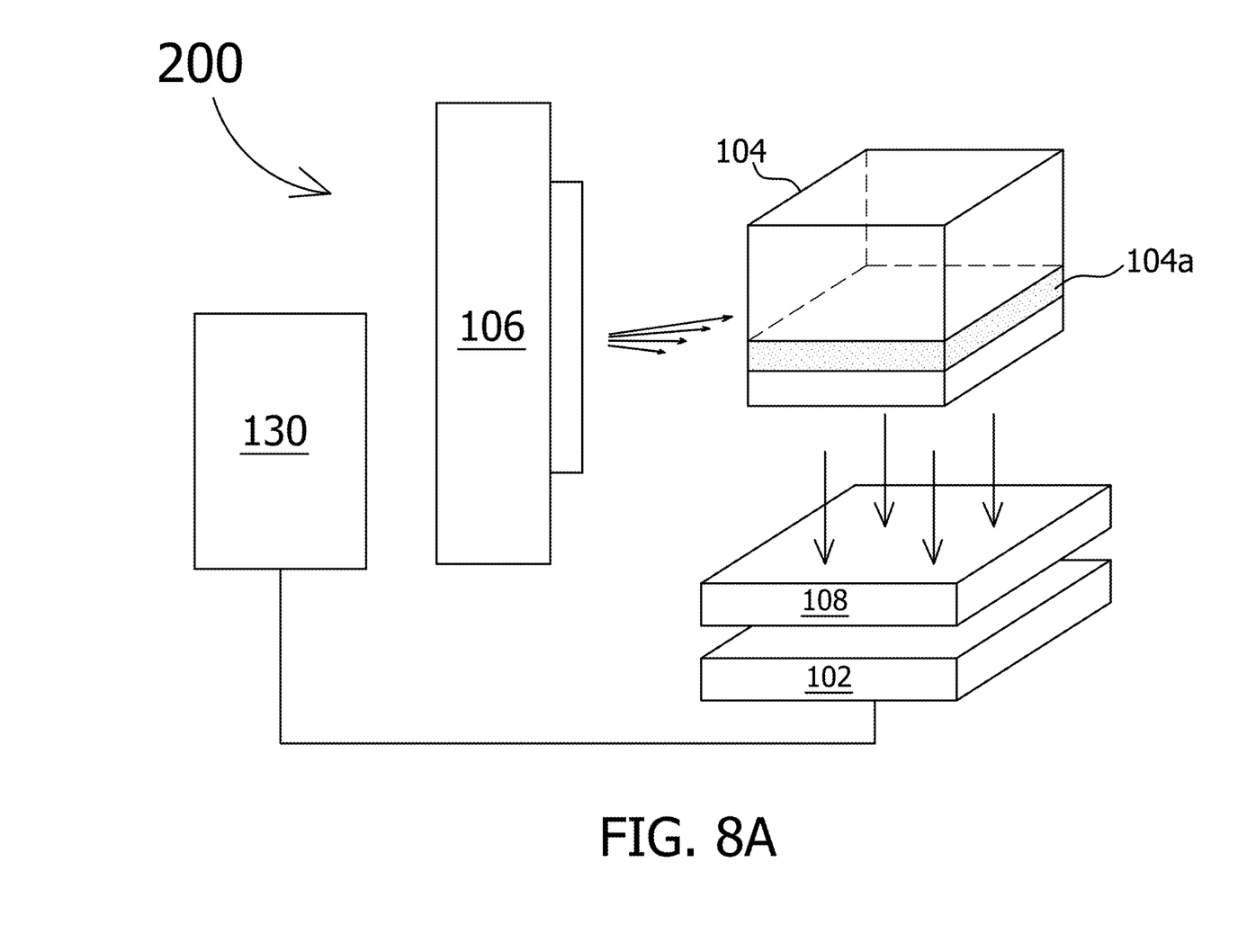
FIG. 8A illustrates a second imaging method, according to an embodiment.
Figure 8B:
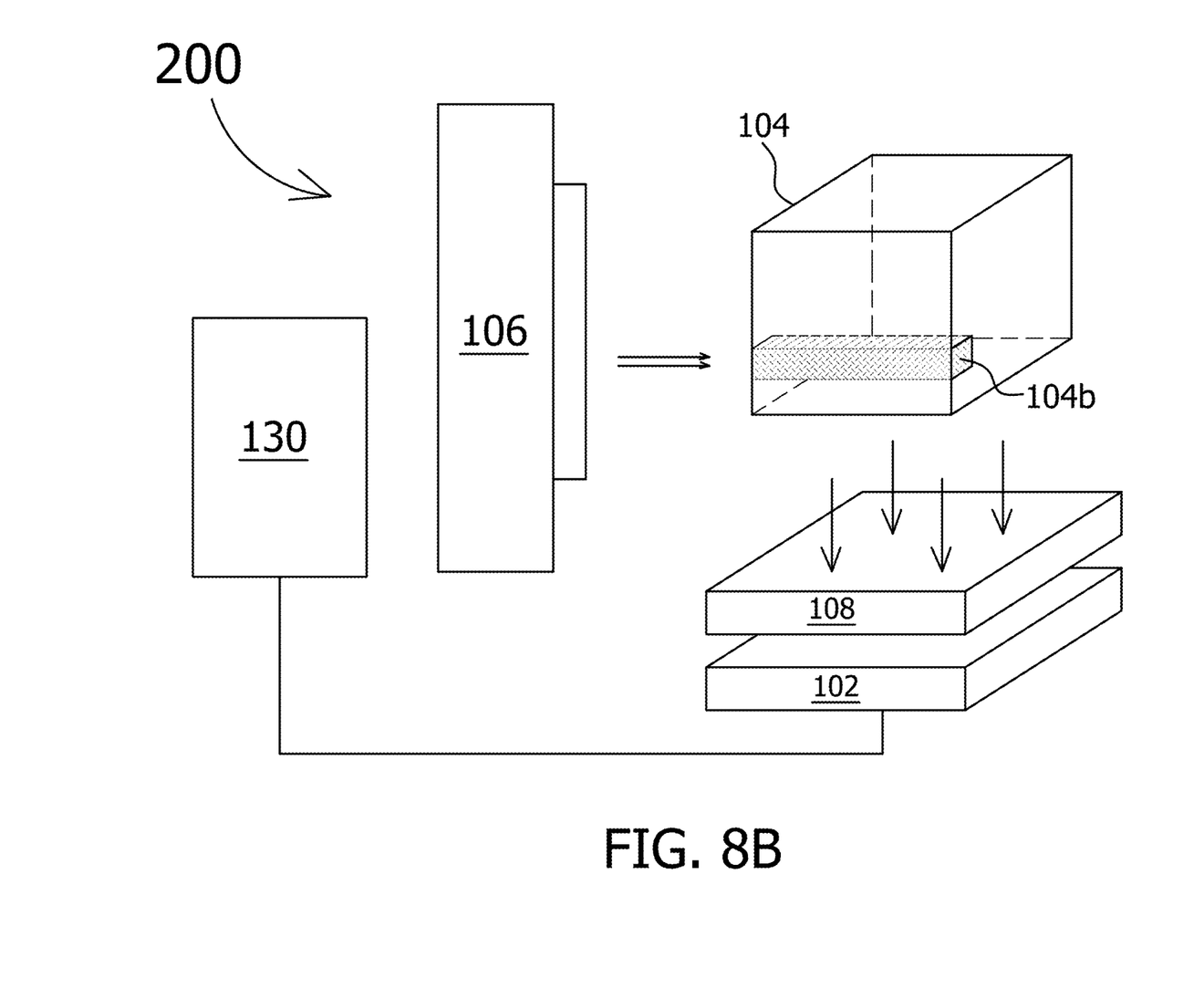
FIG. 8B illustrates a third imaging method, according to an embodiment.

FIG. 8A schematically illustrates a second imaging method for capturing a 3D distribution (also called a 3D image) of the tracer in the object 104, according to an embodiment. In an embodiment, the system 200 used for the second imaging method may include the processor 130, the radiation source 106, the collimator 108, and an X-ray detector 102. In FIG. 8A and FIG. 8B, the object 104 may have the shape of a rectangular box to simplify the description. In general, the object 104 may have any shape.

In an example, the object 104 may be the thyroid of a person. In this example, the tracer may be non-radioactive iodine. Non-radioactive iodine may be present in the thyroid 104 as a result of the non-radioactive iodine being introduced into the body of the person (e.g. injected into the blood stream of the person) and then spreading to the thyroid 104. Alternatively, the non-radioactive iodine may be present in the thyroid 104 by nature.

In an embodiment, the collimator 108 may be positioned between the X-ray detector 102 and the thyroid 104 such that only X-ray photons propagating from the thyroid 104 toward the detector 102 along propagating paths perpendicular to a reference plane intersecting all sensing elements 150 of the detector 102 have a chance of passing through the collimator 108 to reach the detector 102. As a result, X-ray photons propagating from the thyroid 104 toward the detector 102 along propagating paths not perpendicular to the reference plane are blocked and therefore prevented by the collimator 108 from reaching the detector 102.

In an embodiment, for each point of the thyroid 104, a straight line going though that point and perpendicular to the reference plane intersects the detector 102. In other words, the projection area of the thyroid 104 onto the reference plane is within the X-ray detector 102. This means the entire thyroid 104 is in the straight view of the detector 102 as shown in FIG. 8A.

In an embodiment, the thyroid 104 may be deemed to include M imaging slices (including imaging slice 104a for illustration), wherein M is an integer greater than 1. An imaging slice of the thyroid 104 may be a thin, broad piece of the thyroid 104. The broad surfaces of the imaging slice may be planar or curved. The imaging slice may be said to be more confined in one direction in space (e.g., more confined in the z-direction (vertical in FIG. 8A) while less confined in the x-direction and y-direction). In an embodiment, the M imaging slices may be parallel to each other. In an embodiment, the M imaging slices may be parallel to the reference plane.

In an embodiment, the second imaging method may start with a first slice imaging process for the first imaging slice 104a. Specifically, during the first slice imaging process, the non-radioactive iodine in essentially only the first imaging slice 104a of the thyroid 104 may be caused to emit characteristic X-ray photons.

"Essentially only" in this disclosure means "only or almost only". The meaning of "almost only" in this disclosure may be clarified in the following example: the non-radioactive iodine in almost only the imaging slice 104a includes (a) the non-radioactive iodine in the imaging slice 104a and (b) the non-radioactive iodine in small regions outside and adjacent to (i.e., in direct physical contact with) the imaging slice 104a. In other words, almost only the imaging slice 104a may include (a) the imaging slice 104a itself and (b) small regions of the object 104 outside and adjacent to the imaging slice 104a.

In an embodiment, the first slice imaging process may be carried out by using the radiation source 106 to send a first slice excitation radiation (e.g., X-rays or gamma rays or subatomic particles) through essentially only the first imaging slice 104a causing the non-radioactive iodine in essentially only the first imaging slice 104a to emit the characteristic X-ray photons.

In an embodiment, the collimator 108 may be present and positioned such that only the emitted characteristic X-ray photons propagating toward the detector 102 along propagating paths perpendicular to the reference plane may pass through the collimator 108 and hit the sensing elements 150 of the detector 102. Receiving these incident characteristic X-ray photons emitted by the non-radioactive iodine in essentially only the first imaging slice 104a, the detector 102 captures a first slice image of the non-radioactive iodine in essentially only the first imaging slice 104a.

Next, in an embodiment, after the first slice imaging process for the first imaging slice 104a is performed, M−1 slice imaging processes for the remaining M−1 imaging slices of the thyroid 104 are performed sequentially in a similar manner. "Sequentially" (or "in sequence" if any) in this disclosure means one at a time and does not mean any particular order of execution. Here, "sequentially" means that the M slice imaging processes are to be performed one process at a time and does not mean that the M slice imaging processes are to be performed in any particular order. In total, the detector 102 captures M slice images of the non-radioactive iodine in the M imaging slices of the thyroid 104.

Next, in an embodiment, these M slice images may be processed to determine a 3D distribution of the non-radioactive iodine in the thyroid 104. In an embodiment, this processing may be performed using the processor 130 of the system 200. As a result, a physician may examine the 3D distribution of the non-radioactive iodine in the thyroid 104 to learn about the thyroid 104.

FIG. 8B schematically illustrates a third imaging method for capturing a 3D distribution of non-radioactive iodine in the thyroid 104 of the person, according to an embodiment. In an embodiment, the third imaging method may be similar to the second imaging method described above except that in the third imaging method, the thyroid 104 may be deemed to include N imaging bars (including imaging bar 104b for illustration), wherein N is an integer greater than 1. An imaging bar of the thyroid 104 may be a long, straight piece of the thyroid 104. The imaging bar may be said to be more confined in 2 directions in space (e.g., more confined in the y-direction and z-direction while less confined in the x-direction). In an embodiment, the N imaging bars are parallel to each other. In an embodiment, the N imaging bars may be parallel to the reference plane (which intersects all sensing elements 150 of the detector 102).

In an embodiment, the third imaging method may start with a first bar imaging process for the first imaging bar 104b. Specifically, during the first bar imaging process, the non-radioactive iodine in essentially only the first imaging bar 104b of the thyroid 104 may be caused to emit characteristic X-ray photons.

In an embodiment, the first bar imaging process may be carried out by using the radiation source 106 to send a first bar excitation radiation (e.g., X-rays or gamma rays or subatomic particles) through essentially only the first imaging bar 104b causing the non-radioactive iodine in essentially only the first imaging bar 104b of the thyroid 104 to emit the characteristic X-ray photons In an embodiment, the collimator 108 may be present and positioned such that only the emitted characteristic X-ray photons propagating toward the detector 102 along propagating paths perpendicular to the reference plane may pass through the collimator 108 and hit the sensing elements 150 of the detector 102. Receiving these incident characteristic X-ray photons emitted by the non-radioactive iodine in essentially only the first imaging bar 104b, the detector 102 captures a first bar image of the non-radioactive iodine in essentially only the first imaging bar 104b.

Next, in an embodiment, after the first bar imaging process for the first imaging bar 104b is performed, N−1 bar imaging processes for the remaining N−1 imaging bars of the thyroid 104 are performed sequentially in a similar manner. In total, the detector 102 captures N bar images of the non-radioactive iodine in the N imaging bars of the thyroid 104.

Next, in an embodiment, these N bar images may be processed to determine a 3D distribution of the non-radioactive iodine in the thyroid 104. In an embodiment, this processing may be performed using the processor 130 of the system 200.

Figure 8C:
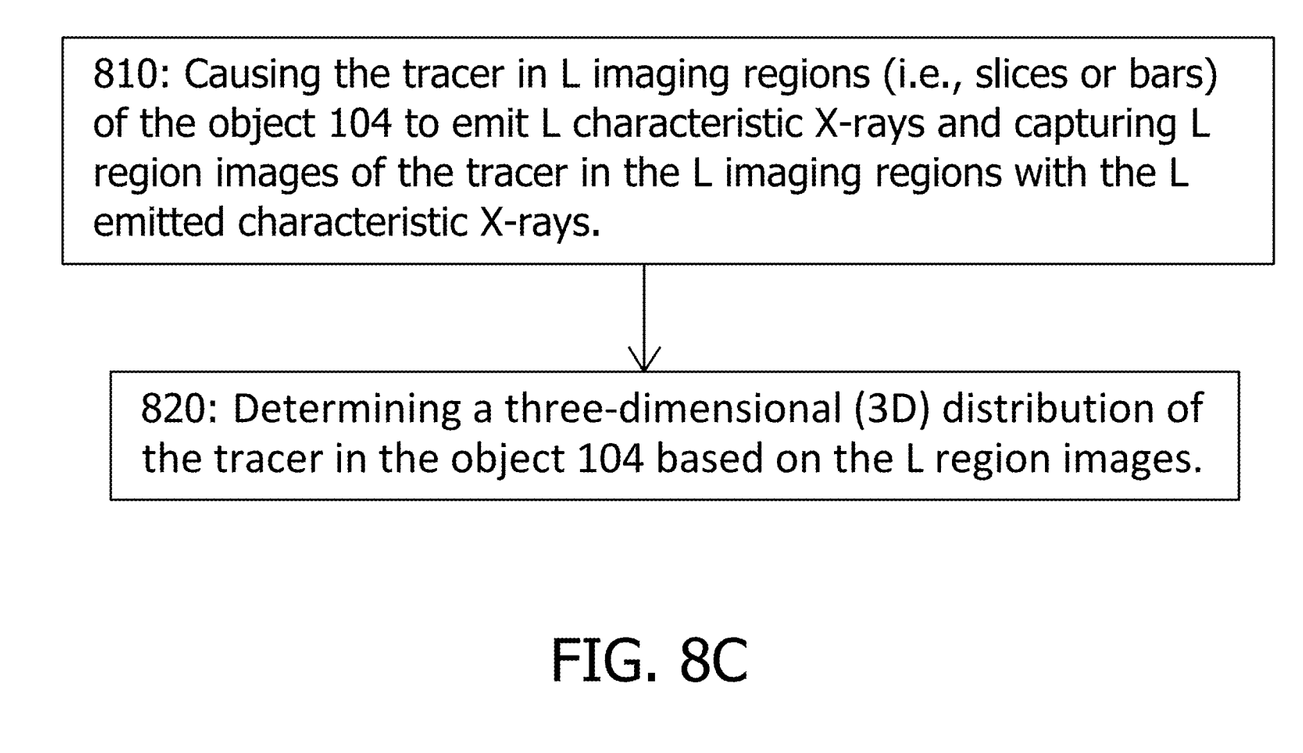
FIG. 8C shows a flowchart summarizing and generalizing the second and third imaging methods.

FIG. 8C shows a flowchart summarizing and generalizing the second and third imaging methods described above. Specifically, with reference to FIG. 8A, FIG. 8B, and FIG. 8C, in step 810, for each one imaging region (i.e., imaging slice or imaging bar) of the total of L imaging regions of the object 104 at a time (L being an integer greater than 1), the tracer in essentially only that imaging region may be caused to emit characteristic X-rays, and a region image of the tracer in essentially only that imaging region may be captured with the emitted characteristic X-rays. The radiation source 106 may be used to send an excitation radiation to essentially only that imaging region causing the tracer in essentially only that imaging region to emit the characteristic X-rays. The X-ray detector 102 may be used to capture the region image.

In an embodiment, the L excitation radiations being sent to the L imaging regions may be fan beams of radiations (the L imaging regions are imaging slices). In an embodiment, the L excitation radiations being sent to the L imaging regions may be cone beams of radiations (the L imaging regions are imaging bars). In an embodiment, the L excitation radiations being sent to the L imaging regions may be collimated beams of radiations (the L imaging regions are imaging bars).

In step 820, a 3D distribution of the tracer in the object 104 may be determined based on the L captured region images. In an embodiment, the steps 810 and 820 may be repeated multiple times over time to create more 3D distributions of the tracer in the object 104 over time. Examining these 3D images, a person may learn how the tracer moves in the object 104 as time progresses.

In the embodiments described above with respect to the second and third imaging methods (FIG. 8A, FIG. 8B, and FIG. 8C), the collimator 108 is used. Alternatively, the collimator 108 may be omitted.

In the embodiments described above with respect to the second and third imaging methods (FIG. 8A, FIG. 8B, and FIG. 8C), non-radioactive iodine is used as a tracer in the thyroid 104 of the person. In an alternative embodiment, radioactive iodine or a mixture of radioactive iodine and non-radioactive iodine may be used as a tracer in the thyroid 104.

In the embodiments described above with respect to the second and third imaging methods (FIG. 8A, FIG. 8B, and FIG. 8C), the object 104 is the thyroid of a person. In general, the object 104 may be a body region of an organism. For example, the object 104 may be a body region right under the skin of a person. In this example, a tracer containing aluminum instead of iodine inside the body region may be of interest (i.e., a 3D distribution of the aluminum tracer in the body region may need to be determined).

In some embodiments described above with respect to the second imaging method (FIG. 8A), the M imaging slices are parallel to each other and to the reference plane. In an alternative embodiment, the M imaging slices are parallel to each other but are not parallel to the reference plane.

In some embodiments described above with respect to the third imaging method (FIG. 8B), the N imaging bars are parallel to each other and to the reference plane. In an alternative embodiment, the N imaging bars are parallel to each other but are not parallel to the reference plane.

In the embodiments described above with respect to the second and third imaging methods as summarized in FIG. 8C, in step 810, for each imaging region (slice/bar) of the thyroid 104 at a time, the imaging process for that imaging region may be carried out by sending an excitation radiation (e.g., X-rays or gamma rays or subatomic particles) through essentially only that imaging region so as to cause the iodine in essentially only that imaging region to emit characteristic X-rays. In general, any method (including exposing iodine in essentially only that imaging region to excitation radiation as described above) may be used to cause iodine in essentially only that region to emit characteristic X-rays.

In an embodiment, if iodine is not present in that imaging region, then (a) iodine may be deemed to be present in that imaging region but its amount is zero, (b) the resulting characteristic X-ray photons emitted by iodine in that imaging region may be deemed to be present but their number is zero, and (c) the captured image of iodine in that imaging region should simply show no trace of iodine.

Figure 9:
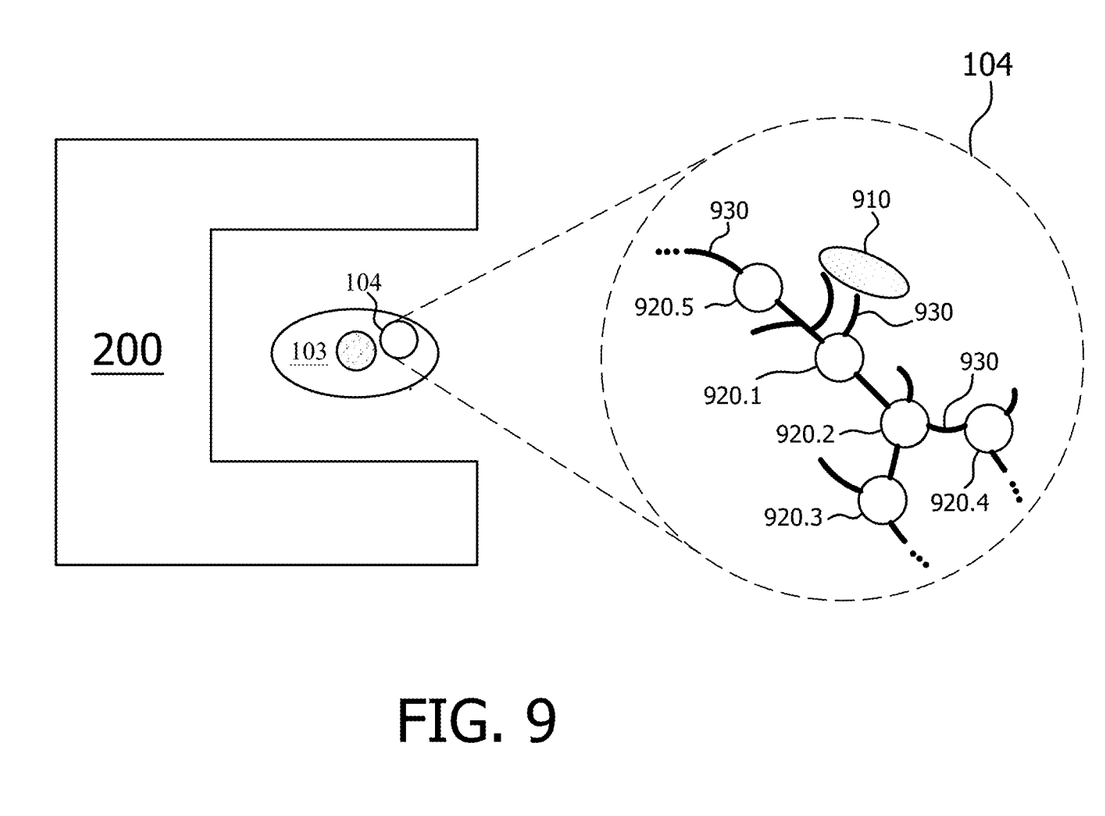
FIG. 9 illustrates the use of the first, second, and third imaging methods to help identify one or more sentinel lymph nodes, according to an embodiment.

FIG. 9 schematically shows the use of any one of the first, second, and third imaging methods (FIG. 7 & FIG. 8C) to help locate/identify one or more sentinel lymph nodes, according to an embodiment.

Specifically, assume that a person 103 has a tumor 910 in the person's breast region 104. Assume further that the breast region 104 includes illustratively 5 lymph nodes 920.1, 920.2, 920.3, 920.4, and 920.5 and lymphatic vessels 930, and that the direction of the lymph flow in the lymphatic vessels 930 is from the lymph node 920.5 to the lymph node 920.1 and then to the lymph node 920.2, and then to the lymph nodes 920.3 and 920.4. As a result, if cancer cells are to spread from the tumor 910, then it is likely that they would travel with the lymph flow through the lymphatic vessels 930 to spread first to the lymph node 920.1 (because the lymphatic vessels 930 closest to the tumor 910 drain first to the lymph node 920.1). Therefore, the lymph node 920.1 is considered the sentinel lymph node for the tumor 910. After that, it is likely that cancer cells would continue to travel with the lymph flow through the lymphatic vessels 930 to spread next to the lymph node 920.2 and then to the lymph nodes 920.3 and 920.4.

Assume it is diagnosed that the tumor 910 has a high risk of being malignant (cancerous). Then, the treatment of the tumor 910 may start with removing the tumor 910. In addition, in order to find out whether cancer has spread from the tumor 910, the sentinel lymph node 920.1 may also be removed in the same operation and then sent for testing for cancer (this operation is usually referred to as the sentinel lymph node biopsy). If the test result indicates that the removed sentinel lymph node 920.1 is negative for cancer (i.e., no cancer cell is found in the sentinel lymph node 920.1), then it is assumed that cancer has not spread from the tumor 910, and therefore no further cancer treatment is needed. But if the test result indicates that the removed sentinel lymph node 920.1 is positive for cancer (i.e., cancer cells are found in the sentinel lymph node 920.1), then it is assumed that cancer has spread from the tumor 910, and therefore further cancer treatment is needed. As an example of additional cancer treatment, the surrounding lymph nodes 920.2, 920.3, 920.4, and 920.5 may also be removed.

In the sentinel lymph node biopsy described above, the sentinel lymph node 920.1 for the tumor 910 need to be identified so that the sentinel lymph node can be removed and sent for testing for cancer. In an embodiment, any one of the first, second, and third imaging methods (FIG. 7 & FIG. 8C) may be used to help locate/pinpoint/identify the sentinel lymph node 920.1 for the tumor 910 as follows.

Firstly, in an embodiment, before any one of the first, second, and third imaging methods is used, a tracer may be introduced into the body of the organism 103 (e.g., a person). The tracer may be non-radioactive. In an embodiment, the tracer may be introduced into the person's body at an introduction site being at (or near) the tumor 910. In an embodiment, the tracer may be introduced into the person's body by injection.

Next, in an embodiment, after the tracer is introduced into the body of the organism 103 (e.g., a person), any one of the first, second, and third imaging methods may now be used to help pinpoint/identify the sentinel lymph node for the tumor 910. Specifically, any one of the first, second, and third imaging methods may be used with the system 200 to sequentially obtain 3D distributions (i.e., 3D images) of the tracer in the breast region 104 as described above with reference to FIG. 7 & FIG. 8C. Examining one or more of these obtained 3D distributions, a physician may be able to pinpoint/identify the sentinel lymph node for the tumor 910.

More specifically, assume that the physician examines a first 3D distribution of the tracer in the breast region 104 and finds that the tracer has spread from the introduction site to some lymphatic vessels 930 near the introduction site but has not spread to any lymph node yet. Assume that the physician then examines a second 3D distribution (which is chronologically after the first 3D distribution chronologically) of the tracer in the breast region 104 and finds that the tracer has spread not only to some lymphatic vessels 930 near the introduction site but also to a first lymph node 920.1. As a result, the physician may identify this first lymph node (920.1) as the sentinel lymph node for the introduction site. Because the introduction site is at the tumor 910, this first lymph node (920.1) is also the sentinel lymph node for the tumor 910. In general, the sentinel lymph node for a site of an organism (e.g., a person, an animal) may be defined as the first lymph node which free entities (e.g., free cancer cells, injected chemical atoms, lymph atoms, etc.) traveling from the site with the lymph flow through the lymphatic vessels would spread first to.

Assume that the physician then examines a third 3D distribution (which is chronologically after the second 3D distribution) of the tracer in the breast region 104 and finds that the tracer has spread not only to the lymphatic vessels 930 near the introduction site and then to the first lymph node (920.1) but also to a second lymph node (920.2). This confirms the physician's earlier identification that the first lymph node (920.1) is the sentinel lymph node for the tumor 910. With the identification of the sentinel lymph node (920.1) for the tumor 910 as described above, the physician may remove the sentinel lymph node (920.1) and then send it for testing for cancer.

In short, with reference to FIG. 9, the identification of the sentinel lymph node for the tumor 910 may be summarized and generalized as follows. Firstly, a tracer is introduced into a body region 104 (e.g., a breast region) of an organism 103 (e.g., a person) at an introduction site being at (or near) a malignant region 910 (e.g., a tumor). Next, any one of the first, second, and third imaging methods (described above) may be used to sequentially determine 3D distributions of the tracer in the body region 104. As a result, these obtained 3D distributions show how the tracer spreads from the introduction site through the lymphatic vessels 930 to the lymph nodes 920 in the body region 104 as time progresses. Therefore, examining one or more of these 3D distributions of the tracer in the body region 104, a physician may be able to identify the sentinel lymph node for the introduction site and also for the malignant region 910. The physician may then remove the sentinel lymph node and send it for testing for cancer.

In the embodiments described above with respect to sentinel lymph node biopsy (FIG. 9), the tumor 910 and the introduction site are in the body region to be imaged (i.e., in the breast region 104). Alternatively, the tumor 910 and the introduction site may be outside the body region to be imaged (i.e., outside the breast region 104).

In the embodiments described above with respect to sentinel lymph node biopsy (FIG. 9), any one of the first, second, and third imaging methods may be used to help pinpoint/identify the sentinel lymph node 920.1 for the tumor 910 in the organism 103 (e.g., a person). In general, any one of the first, second, and third imaging methods may be used to help pinpoint/identify the sentinel lymph node for a malignant region (e.g., a melanoma, a tumor, etc.) of an organism (e.g., a person or an animal).

In the embodiments described above with respect to the sentinel lymph node biopsy (FIG. 9), multiple 3D distributions of the tracer in the breast region 104 may be determined, and then one or more of these 3D distributions may be examined to identify the sentinel lymph node for the tumor 910. Alternatively, a first 3D distribution of the tracer in the breast region 104 may be determined and then examined to identify the sentinel lymph node for the tumor 910. If the sentinel lymph node is not identified in the first 3D distribution, then a second 3D distribution of the tracer in the breast region 104 may be determined and then examined to identify the sentinel lymph node for the tumor 910. If the sentinel lymph node is not identified in the second 3D distribution, then a third 3D distribution of the tracer in the breast region 104 may be determined and then examined to identify the sentinel lymph node for the tumor 910, and so on until the sentinel lymph node for the tumor 910 is identified.

In the embodiments described above with respect to FIG. 9, it is decided that one lymph node (920.1) needs to be removed and sent for testing for cancer. As a result, a sentinel lymph node (920.1) for the tumor 910 needs to be identified. In general, it may be decided that K lymph nodes need to be removed and sent for testing for cancer (K is a positive integer). As a result, K sentinel lymph nodes for the tumor 910 need to be identified. The case K=1 is already described above.

In the case K=2, two lymph nodes for the tumor 910 need to be identified, removed, and then sent for testing for cancer. In the description above, the physician examines the third 3D distribution of the tracer in the breast region 104 and finds that the tracer has spread not only to the lymphatic vessels 930 near the introduction site and to the first lymph node (920.1) but also to a second lymph node (920.2). As a result, the physician may identify the first and second lymph nodes (920.1 & 920.2) as the 2 sentinel lymph nodes for the tumor 910 and may remove these 2 sentinel lymph nodes and send them for testing for cancer. In an embodiment, if at least one of the 2 sentinel lymph nodes is positive for cancer, then it may be assumed that cancer has spread from the tumor 910, and therefore further cancer treatment is needed.

In the embodiments described above with respect to FIG. 9, the entire sentinel lymph node 920.1 is removed for testing for cancer. In general, a sample may be removed from the sentinel lymph node 920.1 and then sent for testing for cancer. The sample may comprise only a portion of the sentinel lymph node 920.1 or the entire sentinel lymph node 920.1.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
    introducing a tracer into a body region of an organism at an introduction site of the organism, wherein the body region comprises L imaging regions (imaging regions (i), i=1, . . . , L), and wherein L is an integer greater than 1;
    for i=1, . . . , L, causing the tracer in essentially only the imaging region (i) to emit characteristic X-ray photons (i);
    for i=1, . . . , L, capturing a region image (i) of the tracer in essentially only the imaging region (i) with the characteristic X-ray photons (i);
    determining a first 3D distribution of the tracer in the body region based on the region images (i), i=1, . . . , L; and
    examining the first 3D distribution of the tracer in the body region to identify a sentinel lymph node for the introduction site.

2. The method of claim 1, further comprising, in response to the sentinel lymph node being not identified in the first 3D distribution:
    repeating said causing, said capturing, and said determining thereby resulting in a second 3D distribution of the tracer in the body region; and
    examining the second 3D distribution of the tracer in the body region to identify the sentinel lymph node.

3. The method of claim 2, further comprising, in response to the sentinel lymph node being not identified in the second 3D distribution:
    repeating said causing, said capturing, and said determining thereby resulting in a third 3D distribution of the tracer in the body region; and
    examining the third 3D distribution of the tracer in the body region to identify the sentinel lymph node.

4. The method of claim 1, wherein the introduction site is in a malignant region of the organism.

5. The method of claim 1, wherein the organism is a person.

6. The method of claim 1, further comprising, in response to the sentinel lymph node being identified:
    removing a sample from the sentinel lymph node; and
    testing the sample for cancer.

7. The method of claim 6, further comprising removing additional lymph nodes surrounding the sentinel lymph node in response to cancer being found in the sample as a result of said testing.

8. The method of claim 1, wherein said causing the tracer in essentially only the imaging region (i) to emit the characteristic X-ray photons (i) comprises irradiating imaging region (i) with excitation radiation (i).

9. The method of claim 8, wherein the excitation radiation (i) comprises X-rays or gamma rays.

10. The method of claim 1, wherein the tracer is non-radioactive.

* * * * *